United States Patent [19]

Drago et al.

[11] Patent Number: 4,943,644
[45] Date of Patent: Jul. 24, 1990

[54] OLEFIN AND ALKANE OXIDATIONS, RUTHENIUM CARBOXYLATE CATALYST THEREFOR AND METHOD OF PREPARATION THEREOF

[75] Inventors: Russell S. Drago; Shannon Davis, both of Gainesville, Fla.

[73] Assignee: The University of Florida, Gainesville, Fla.

[21] Appl. No.: 274,837

[22] Filed: Nov. 23, 1988

Related U.S. Application Data

[62] Division of Ser. No. 147,302, Jan. 22, 1988, Pat. No. 4,885,377.

[51] Int. Cl.$^5$ ............................................. C07D 301/06
[52] U.S. Cl. .................................... 549/533; 568/360; 568/431; 568/475; 568/836
[58] Field of Search ............... 568/475, 431, 360, 836; 541/533

[56] References Cited

U.S. PATENT DOCUMENTS 3,993,672  11/1976  Arzoumanian et al. ............ 549/533

FOREIGN PATENT DOCUMENTS 50-7  1/1975  Japan ................................ 549/533

OTHER PUBLICATIONS

Drags et al., Inorg. Chem., vol. 21, p. 2196 (1982).
Doyle et al., Inorg. Chem., vol. 23, p. 3684 (1984).
Bilgrien et al., J.A.C.S., vol. 109, p. 3786 (1987).

*Primary Examiner*—James H. Reamer
*Attorney, Agent, or Firm*—Dennis P. Clarke

[57] ABSTRACT

A method of oxidizing olefins or alkanes by contacting with oxygen and a catalyst composition of the formula:

$$Ru_3O[OCO(CF_2)_yCF_3]_6L$$

Wherein: Ru are reuthenium atoms having a formal oxidation state of +2 or +3,
L is a neutral or anionic ligand,
Y is an integer from 0 to 6, and
x is an integer from 1 to 3; and an anion.

1 Claim, No Drawings

OLEFIN AND ALKANE OXIDATIONS, RUTHENIUM CARBOXYLATE CATALYST THEREFOR AND METHOD OF PREPARATION THEREOF

This is a Divisional of application Ser. No. 147,302, filed Jan. 22, 1988, now U.S. Pat. No. 4,885,377.

BACKGROUND OF THE INVENTION

1. Field of the Invention

The present invention relates to novel olefin oxidation catalysts. Work leading to the present invention was conducted under National Science Foundation Grant No. 86 18766.

2. Prior Art

It is known to oxidize olefins with oxygen to produce oxygenated derivatives at the olefinic double bond, e.g., epoxides, or to cleave the olefinic double bond to yield aldehydes, alcohols, etc. It is also known to oxidize cyclic alkanes with $O_2$ to produce alcohols and ketones.

It has been attempted to optimize these methods by carrying out the oxidations in the presence of catalysts. Ethylene has been converted to ethylene oxide over a supported silver oxide catalyst [Kitty et al, Cat. Rev., Vol. 10, p. 1 (1974)]. Catalyzed norbornene oxidations are described by Taylor et al, J.A.C.S., Vol. 109, p. 2770 (1987); Taylor et al, J.A.C.S., Vol. 108, p. 2782 (1986); olefin epoxidations, Bailey et al, Chem. Comm., 179 (1987), Balavoine et al, Tett. Letters, Vol. 25, p. 3187 (1984) and Meunier, Bull. Chem. Soc. France, 578 (1986). Cyclohexane is presently commercially oxidized to adipic acid using cobalt (II) napthenoate as a catalyst. [Berezin et al, "The Oxidation of Cyclohexane", Pergamon Press: Oxford, 1966)]. Common catalysts for such oxidations include silver/silver oxide, cobalt (II) napthenoate, vanadates, molybdates etc.

The disadvantages inherent in these known oxidation methods are that they require relatively high temperatures and pressures and the reaction media are highly corrosive.

Although previous studies of the fundamental chemistry of trinuclear ruthenium carboxylate complexes have appeared in the literature [Cotton et al, J. Chem. Soc. Chem. Comm., 967 (1971); Spencer et al, J. Chem. Soc., Dalton Trans., 1570 (1972); ibid, 786 (1974); Cotton et al, Inorg. Chem. Acta., Vol. 6, p. 411 (1972); Wilson et al, J. Am. Chem. Soc., Vol. 97, p. 2285 (1975); Baumann et al, Inorg. Chem., Vol. 17, p. 3342 (1978); Baumann et al, Inorg. Chem., Vol. 18, p. 2472 (1979) and Walsh et al, Inorg. Chem., Vol. 18, p. 2472 (1979)], it is only in the past few years that these compounds have been utilized as catalysts [Legzdins et al, J. Chem. Soc., Dalton Trans., 3322 (1970); Mitchell et al, J. Chem. Soc., Dalton Trans., 846 (1973); Sasson et al, Tetrahedron Lett., Vol. 47, p. 4133 (1974); Sasson et al, Can. J. Chem., Vol. 52, p. 3825 (1974); Fouda et al, Inorg. Chem., Vol. 17, p. 3213 (1978); Milner et al, J. Organomet. Chem., Vol. 152, p. 193 (1979); Fouda et al, Inorg. Chem., Vol. 18, p. 1 (1979); Sasson et al, J. Mol. Catal., Vol. 6, p. 289 (1979); Trzeciak et al, J. Oxid. Comm., Vol. 1, p. 295 (1980); Trzeciak et al, J. Mol. Catal., Vol. 10, p. 69 (1981); Carlsen et al, J. Org. Chem., Vol. 46, p. 3936 (1981); Shibaeva et al, Vestsi Akad. Navuk BSSR, Ser. Khim. Navuk, 40 (1982); Thivolle-Cazat et al, J. Chem. Soc., Chem. Commun., 1128 (1982); Ito et al, Tetrahedron Lett., Vol. 24, p. 5249 (1983); Nicolaides et al, J. Mol. Catal., Vol. 24, p. 375 (1984) and Trzeciak et al, J. Mol. Catal., Vol. 39, p. 85 (1987). A recent report [Bilgrien et al, J. Amer. Chem. Soc., Vol. 109, p. 3786 (1987)] that $Ru_3O(O_2CR)_6L_3{}^n$ ($R=CH_3$, $C_2H_5$; $L=H_2O$, $PPh_3$; $n=0$, $+1$) is an efficient catalyst for the selective oxidation of primary and secondary alcohols to aldehydes and ketones using molecular oxygen as the oxidant is the only reported instance of $O_2$ activation by these trimers. This result encouraged attempts to use this complex as a catalyst for other substrates; however, attempts to oxidize olefins were unsuccessful. Rhodium carboxylate dimers showed intriguing differences in acidity [Drago et al, Inorg. Chem., Vol. 21, p. 2196 (1982) when carboxylate ligands were exchanged for fluorinated carboxylates, including the reported [Doyle et al, Inorg. Chem., Vol. 23, p. 3684 (1984) ability of the trifluoroacetate dimer to bind olefins. Previous attempts to prepare ruthenium trifluoroacetate trimer were unsuccessful [Spencer et al, supra].

It is an object of the present invention to provide novel complexes useful as olefin oxidation catalysts, a method for their preparation and an improved olefin or alkane oxidation method utilizing the complexes of the invention.

SUMMARY OF THE INVENTION

The above and other objects are realized by the present invention which provides a composition of matter comprising a cation of the formula:

Wherein: Ru are ruthenium atoms having a formal oxidation state of $+2$ or $+3$, L is a neutral or anionic ligand, y is an integer from 0 to 6, and x is an integer from 1 to 3; and an anion.

According to a further embodiment of the invention, there is also provided a method of preparing a composition of matter comprising a cation of the formula:

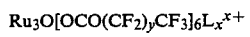

Wherein: Ru are ruthenium atoms having a formal oxidation state of $+2$ or $+3$, L is a neutral or anionic ligand, y is an integer from 0 to 6, and x is an integer from 1 to 3;

and an anion, the method comprising reacting a complex of the formula:

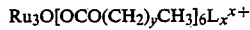

with a compound selected from the group consisting of $CH_3(CF_2)_yCOOH$, the anhydride thereof or mixtures of the acid and the anhydride in the presence of the anion.

Finally, according to a still further embodiment of the invention, there is provided an improved method of oxidizing olefins wherein the olefin is contacted with oxygen in the presence of a catalyst for a time sufficient to oxidize an olefinic double bond therein, the improvement comprising conducting the oxidation in the presence of a catalyst comprising the above described complex.

DETAILED DESCRIPTION OF THE INVENTION

The complexes of the invention may be prepared by refluxing the appropriate alkanoate analog described above with, preferably, a mixture of the perfluoric acid and its anhydride for a time sufficient to complete the reaction.

The alkanoate analog may be prepared by refluxing RuCl$_3$·xH$_2$O (ruthenium trichloride trihydrate) in a 1:1 mixture of alcohol and acid in the presence of, e.g., NaOH. After heating under N$_2$ for 4 hours, the mixture is filtered, evaporated to dryness, and dried in vacuo overnight.

The alkanoate may then be refluxed in, e.g., a mixture of perfluoroalkanoic acid and perfluoroalkanoic anhydride. The resulting solution is preferably evaporated to dryness and the resulting solid dissolved in ether and filtered. The resulting solution is evaporated again and dried in vacuo overnight. Proton NMR spectra show the absence of alkanoate ligands and the presence of coordinated ether molecules; $^{19}$F NMR indicates two different kinds of perfluoroalkanoate groups. The IR of the complexes also indicates two kinds of coordinated carboxylate groups. This evidence, combined with the elemental analyses, leads to a general formula for complexes as [Ru$_3$O(pfa)$_6$(Et$_2$O)$_x$]pfa[Ru$_3$O(pfb)$_6$(Et$_2$O)$_x$](pfb) where pfa=perfluorinated alkanoate acid and x=1, 2 or 3 depending on the length of drying time.

Olefin oxidations were carried out in a standard Parr pressure apparatus. The reactions involved 50 ml of solvent (acetonitrile), $10^{-4}$–$10^{-5}$ molar concentration of catalyst, at least an 100-fold excess of substrate, 40 psi O$_2$ initial pressures, and all reactions were held at 65° C. in an oil bath.

The specific olefins used as substrates were (1) cyclohexene, (2) norbornene, and (3) trans-$\beta$-methyl styrene.

In the complexes of the invention, the ligands L may be any neutral or anionic ligand which does not affect the catalytic activity of the resulting complex. Typical such ligands are diethyl ether, water, triphenylphosphine, pyridine, etc.

The anion in the complexes of the invention may comprise any suitable anion which does not conflict with the intended catalytic use of the complex. Typically, the anion will comprise the carboxylate anion of the perfluoro acid used to prepare the complex, but may also comprise another carboxylate, perchlorate, hexafluorophosphate, etc.

The invention is illustrated by the following non-limiting examples.

EXAMPLE 1

Crude Ru$_3$O(prop)$_6$(H$_2$O)$_3$$^+$ (where prop=CH$_3$CH$_2$O$_2$$^-$), prepared as previously described [Bilgrien et al, supra], was refluxed in a 10:1 mixture of perfluorobutyric (pfb) acid and perfluorobutyric anhydride for 30 minutes. The olive-green solution was evaporated to dryness and the resulting solid was dissolved in ether and filtered. The resulting solution was evaporated again and dried under vacuum overnight. Proton NMR spectra showed the absence of all propionate resonances, indicating complete conversion to the fluorinated complex, while $^{19}$F NMR indicates two different kinds of perfluorobutyrate groups (bridging and an anionic counterion). The IR of this complex is decidedly different from that of the starting material; the H$_2$O peak at 3400 cm$^{-1}$ is absent, and the carboxylate stretch occurs at 1704 cm$^{-1}$ as compared with 1567 cm$^{-1}$ [The UV spectrum of the perfluorobutyrate complex also shows a similar shift with a broad absorption at 905 nm and a charge transfer band about 390 nm containing a shoulder at 410 nm compared with the propionate trimer having bands at 670, 610, and 310 nm]. FAB M/S performed on this complex gave a parent ion peak at 1675 mass units, corresponding to a protonated Ru$_3$O(pfb)$_6$(Et$_2$O)$_3$ species. This evidence, combined with the elemental analyses [Calculated for [Ru$_3$O(pfb)$_6$(Et$_2$O)$_{1.5}$][pfb]: % C=21.24, % H=0.78, % F=48.46]. Found (Galbraith Laboratory, Knoxville, TN): % C=21.20, % H=0.73, % F=47.94], leads us to formulate this complex as [Ru$_3$O(pfb)$_6$(Et$_2$O)$_x$](pfb), where x=1, 2 or 3, depending on the length of drying time.

EXAMPLE 2

The perfluorobutyrate complex catalyzes olefin oxidations using molecular oxygen as the oxidant at 65° C. The oxidations were carried out using apparatus previously described [Nyberg et al, J. Am. Chem. Soc., Vol. 105, p. 3538 (1983)], with initial pressures of 40 psi of oxyen. The solutions were $10^{-3}$ to $10^{-4}$ M in catalyst and used at least an 100-fold excess of substrate in acetonitrile solvent. All reactions were periodically monitored by GC and GCMS.

Several different olefins were attempted as substrates. An induction period of 24 hours was observed in the oxidation of norbornene to norbornene oxide, similar to that seen in work reported earlier [Bailey et al, J. Chem. Soc. Chem. Comm., 179 (1987)] utilizing the high-valent oxo-ruthenium complex [Ru(O)$_2$(2,9-dimethyl-1,10-phenanthroline)2]-(PF$_6$)$_2$ or Ru(dmp). The Ru(pfb) complex was only slightly less active than this previously reported catalyst, producing 22 turnovers in 48 hours as compared to 37 turnovers in the same period of time for the Ru(dmp) catalyst.

In the oxidation of cyclohexene, products typical of a free radical autoxidation process were observed after an induction period of about 1 hour. The major products, cyclohexene oxide, the allylic alcohol and ketone, were formed in roughly a 4:16:9 molar ratio after 3 hours; significant amounts of other products were also observed in the GC. The addition of benzoquinone, a free radical trap, completely inhibited the reaction for a finite period, after which the reaction resumed. This suggests that oxidation of the alkene resumes after the oxidation of the quinone is complete.

In order to determine the stereo-selectivity of the reaction, the oxidation of trans-$\beta$-methylstyrene was attempted. This reaction proceeded even more slowly than the previous oxidations, producing only trace amounts of the trans epoxide after 40 hours. The major products of the reaction were those due to the cleavage of the double bond—benzaldehyde and acetaldehyde.

These results lead to the conclusion that the mechanism for these oxidations involves generation of a hydrocarbon radical, hydrogen atom abstraction, reaction of the radical with O$_2$ to form a hydroperoxide, and subsequent Haber-Weiss decomposition of this hydroperoxide.

EXAMPLE 3

The oxidation of 40 ml of cyclohexane at 65° C., 3 atm O$_2$ initial pressure, with $10^{-5}$ molar concentration of the perfluorobutyrate catalyst of the invention in 10 ml acetonitrile as solvent produces as the only products cyclohexanol and cyclohexanone. Approximately 2 turnovers with respect to ketone production were observed in 40 hours of reaction time. Increasing the reaction temperature to 75° C. produced the same two products in significantly higher yield—16 turnovers with respect to ketone in 40 hours. The industrial oxidation of cyclohexane to the alcohol and ketone is normally carried out at 165° C. and 10 atm O₂, substantially harsher conditions than those used according to the present invention.

We claim:

1. In a method of oxidizing olefins or alkanes wherein said olefin is contacted with oxygen in the presence of a catalyst for a time sufficient to oxidize said olefin or alkane, the improvement comprising conducting said oxidation in the presence of a catalyst consisting essentially of a complex of the formula:

$$Ru_3O[OCO(CF_2)_yCF_3]_6L_x{}^{x+}$$

wherein: Ru are reuthenium atoms having a formal oxidation state of +2 or +3,
L is a neutral or anionic ligand,
y is an integer from 0 to 6, and
x is an integer from 1 to 3; and an anion.

* * * * *